United States Patent [19]
Buzzard et al.

[11] Patent Number: 6,162,187
[45] Date of Patent: Dec. 19, 2000

[54] FLUID COLLECTION APPARATUS FOR A SURGICAL DEVICE

[75] Inventors: Jon D. Buzzard, Milford; Thomas E. Albrecht; David D. Beck, both of Cincinnati; John A. Hibner, Mason; Eduardo Salazar, Cincinnati, all of Ohio

[73] Assignee: Ethicon Endo-Surgery, Inc., Cincinnati, Ohio

[21] Appl. No.: 09/365,619

[22] Filed: Aug. 2, 1999

[51] Int. Cl.[7] .............................. A61B 5/00; B65D 81/00
[52] U.S. Cl. ............................................................. 600/573
[58] Field of Search ................................... 600/573, 571

[56] References Cited

U.S. PATENT DOCUMENTS

| | | | |
|---|---|---|---|
| 4,320,761 | 3/1982 | Haddad | 128/305 |
| 4,832,685 | 5/1989 | Haines | 604/30 |
| 4,946,434 | 8/1990 | Plaisted et al. | 494/29 |
| 5,062,774 | 11/1991 | Kramer et al. | 417/413 |
| 5,526,822 | 6/1996 | Burbank et al. | 128/754 |
| 5,649,547 | 7/1997 | Ritchart et al. | 128/754 |
| 5,697,898 | 12/1997 | Devine | 604/22 |
| 5,775,333 | 7/1998 | Burbank et al. | 128/754 |
| 5,885,261 | 3/1999 | Longo et al. | 604/319 |

FOREIGN PATENT DOCUMENTS

WO 99/15079    4/1999    WIPO .

*Primary Examiner*—Max Hindenburg
*Assistant Examiner*—Brian Szmal

[57] ABSTRACT

A fluid collection apparatus is provided for controlling fluid communication between a vacuum source and first and second vacuum lines of a surgical device such as a core sampling biopsy device. The fluid collection apparatus comprises first and second fluid lines adapted for detachably connecting to, and in fluid communication with, the first and second vacuum lines, respectively, of the surgical device. The fluid collection apparatus further comprises first and second valves in fluid communication with first and second fluid lines, respectively. Each of first and second valves has an open position and a closed position. The fluid collection apparatus further comprises an air vent selectively communicating with first and second vacuum lines, and a valve frame for fixing first and second valves relative to each other, where the valve frame has a latching means for detachably connecting the valve frame to the surgical device.

10 Claims, 10 Drawing Sheets

FLUID COLLECTION APPARATUS FOR A SURGICAL DEVICE

RELATED PATENTS AND PATENT APPLICATIONS

This application is related to the following co-pending U.S. patent applications, which are hereby incorporated herein by reference: Ser. No. 08/878,468 filed on Jun. 18, 1997; Ser. No. 09/107,845 filed on Jun. 30, 1998; Ser. No. 09/178,075 filed on Oct. 23, 1998; Ser. No. 09/282,142 filed on Mar. 31, 1999, and Ser. No. 09/282,140 filed on Mar. 31, 1999.

FIELD OF THE INVENTION

The present invention relates, in general, to devices for managing fluids during surgical procedures and, more particularly, to devices for collecting and dispensing fluids in core sampling biopsy probes for acquiring subcutaneous biopsies and for removing lesions.

BACKGROUND OF THE INVENTION

The diagnosis and treatment of patients with cancerous tumors, pre-malignant conditions, and other disorders has long been an area of intense investigation. Non-invasive methods for examining tissue include palpation, X-ray, MRI, CT, and ultrasound imaging. When the physician suspects that a tissue may contain cancerous cells, a biopsy may be done using either an open procedure or a percutaneous procedure. For an open procedure, the surgeon creates a large incision within the tissue in order to provide direct viewing and access to the tissue mass of interest. The entire mass (excisional biopsy) or a part of the mass (incisional biopsy) may then be removed. For a percutaneous biopsy, a needle-like instrument is used through a very small incision to access the tissue mass of interest and to obtain a tissue sample for later examination and analysis. The advantages of the percutaneous method as compared to the open method are significant. The procedure is normally done relatively quickly with local anesthetics. Recovery time and the cost of the procedure are diminished, and there is typically much less disfigurement of the patient's anatomy. In addition, use of the percutaneous method in combination with imaging devices such as X-ray and ultrasound has resulted in highly reliable diagnoses and treatments.

Generally there are two ways to obtain percutaneously a portion of tissue from within the body, by aspiration or by core sampling. Aspiration of the tissue through a fine needle requires the tissue to be fragmented into pieces small enough to be withdrawn in a fluid medium. The method is less intrusive than other known sampling techniques but one can only examine cells in the liquid (cytology) and not the cells and the structure (pathology). In core biopsy, a core or fragment of tissue is obtained for histological examination, which may be done via a frozen or paraffin section. The type of biopsy used depends mainly on various factors present in the patient, and no single procedure is ideal for all cases. Core sampling biopsy, however, is very useful in a number of conditions and is widely used by physicians.

A number of core sampling biopsy devices have been developed and commercialized for use in combination with imaging devices. One example is a core sampling biopsy device known as the MAMMOTOME biopsy device marketed by Ethicon Endo-Surgery, Inc., Cincinnati, Ohio. The MAMMOTOME biopsy device is vacuum-assisted and some of the steps for retrieving multiple tissue samples have been automated. The operator uses this device to capture "actively" (using the vacuum) the tissue prior to severing it from the body. This allows for sampling tissues of varying hardness. In the MAMMOTOME biopsy device, a cutting cannula is rotated using a motor drive mounted in the instrument while the operator manually moves the cutting cannula back and forth by a knob on the outside of the instrument. Thus, the operator is able, through tactile feedback, to determine whether the blade is effectively cutting tissue or if there is a problem, such as binding or stalling. The operator may then adjust the speed at which the blade is moved through the tissue, stop the blade, or back the blade away from the tissue. The device can also be used to collect multiple samples in numerous positions about its longitudinal axis, without removing the biopsy needle from the body. These features allow for substantial sampling of large lesions and complete removal of small ones. In the MAMMOTOME biopsy device, a vacuum chamber is attached alongside and fluidly connected to an elongated, hollow piercing element. The vacuum supplied through the vacuum chamber pulls tissue into a lateral receiving port of the hollow piercing element. This type of vacuum-assisted biopsy device is disclosed in U.S. Pat. No. 5,649,547 issued to Ritchart, et al, on Jul. 22, 1997.

The MAMMOTOME biopsy device may be used with a handheld, real-time imaging ultrasonic device, or with numerous kinds of X-ray stereotactic tables in which the patient may lay down or sit upright. When used with an X-ray stereotactic table, the MAMMOTOME biopsy device is attached to a movable, mechanical mounting arm on the table. For one type of table, the patient lies face down on the table and the patient's breast is positioned in an opening. Several X-ray images of the breast are taken from different angles to determine the location of the suspect tissue. Next the mounting arm is manually repositioned so that the MAMMOTOME biopsy device is properly aligned with the breast. Then the mounting arm is manipulated to push the piercing element of the biopsy device into the breast until the tip of the piercing element is positioned alongside the tissue to be sampled. Additional X-ray images are then made to confirm that the port on the distal end of the piercing element is in the proper position to collect the desired tissue samples. The MAMMOTOME biopsy device is then used to retrieve one or more core samples of tissue. Additional X-ray images are taken to confirm the removal of the suspect tissue. Sometimes the MAMMOTOME biopsy device and mounting arm must be repositioned during the procedure so that the tip of the piercing element is in a new location in order to retrieve more tissue samples.

During a procedure for obtaining numerous tissue core samples using a biopsy device such as the MAMMOTOME biopsy device, a substantial amount of fluids must be communicated to and from the tissue-sampling site within the patient's body. Each time the piercing element and/or the cutting cannula are withdrawn from the body to transport the tissue sample for removal from the distal end of the cannula, fluids can escape from the tissue through the biopsy device. In the MAMMOTOME biopsy device, a knockout tube is provided so that as the cutting cannula is withdrawn from the tissue and the distal end of the cutting cannula is outside the body, the distal end of the knockout tube pushes out the core sample automatically from the distal end of the cutting cannula. A drain line is attached to the proximal end of the knockout tube so that fluids contained in the cutting cannula can be removed. This drain line may be attached to a vacuum source to remove the fluids more effectively. Sometimes the operator wishes to disconnect the drain line from the knockout tube in order to inject an additional amount of anesthetic solution (such as lidocaine) into the tissue mass to insure that a sufficient amount is present at the area where the tissue sample will be taken. By removing this drain line, the fluid within the tissue, which may be at a relatively high pressure, can escape from the device. The knockout tube (also referred to as a knockout pin) is disclosed also in U.S. Pat. No. 5,649,547 (Ritchart). The knockout tube and the vacuum chamber are attached to separate vacuum lines fluidly connected to a vacuum source.

Two vacuum lines for removing fluids are also required for another vacuum-assisted, core sampling biopsy device disclosed in PCT international application WO 99/15079 by Farascioni, et al, and published on Apr. 1, 1999. During set-up for this biopsy device, it is also necessary to attach separately each of the two vacuum lines to a vacuum source. After the biopsy procedure is completed, these fluid carrying lines must be drained and removed in order to clean the biopsy device, vacuum source, etc. and set-up a new, sterile set of fluid carrying tubes for the next patient. Any measures, therefore, to facilitate the attachment of these vacuum lines, in both the MAMMOTOME biopsy device and the Farascioni device, will help to shorten the set-up time and prevent spillage of fluids in the surgical environment.

Various disposable, fluid collection devices have been developed in other medical arts for relatively easy set-up and takedown for each patient. For example, a disposable manifold and valve for processing of blood is disclosed in U.S. Pat. No. 4,946,434 issued to Plaisted, et al on Aug. 7, 1990. Similarly, a solution pumping system including a disposable pump cassette is disclosed in U.S. Pat. No. 5,062,774 issued to Kramer, et al, on Nov. 5, 1991. An autotransfusion system and method is disclosed in U.S. Pat. No. 5,885,261 issued to Longo, et al on Mar. 23, 1999. Fluid collection systems are also disclosed for use with surgical devices for phacoemulsification and removal of cataract lens. Examples include U.S. Pat. No. 5,697,898 issued to Devine, et al on Dec. 16, 1997, and U.S. Pat. No. 4,832,685 issued to Haines, et al, on May 23, 1989. All these devices and methods combine the disposable fluid carrying components in a way to allow for easy set-up/takedown, but they are not designed for the type of two-vacuum line fluid collection system required for the aforementioned biopsy devices.

As described in the related patent applications referenced earlier, it is also highly desirable to automate the operation of the core sampling biopsy device to reduce the time of the procedure, insure the correct sequence of steps, and reduce the need for assistance in carrying out the procedure. An automated fluid collection apparatus is especially advantageous in controlling the flow of fluids to and from the biopsy device. It is not necessary, for example, to have a vacuum source continuously supplying vacuum to the biopsy device. Therefore, an "on-off" valve in the vacuum lines connected to the biopsy device may be operated by a control unit programmed for supplying vacuum only during certain steps of the operational sequence. Also, it may be desirable to pulse the vacuum pressure supplied to the vacuum lines in order to free tissue debris which may be lodged in the biopsy device, and this pulsing could be provided by an automated valve actuator responding to an operator command. For biopsy devices having more than one vacuum line such as the MAMMOTOME biopsy device, it is desirable to be able to control automatically the flow of fluids through each line independently. This is important, for example, when it is desired to remove a tissue sample from a patient. Vacuum supplied to the vacuum chamber for pulling the tissue sample into the lateral receiving port must first be "turned off" before the tissue sample can be moved from the distal end of the hollow piercing element to outside the patient's body by retracting the cutting cannula. Vacuum is maintained within a lumen in the cutting cannula to help hold the tissue sample inside the lumen while the cutting cannula is retracted. Therefore, it is important to have independent means for supplying vacuum and ambient pressure to the vacuum chamber and to the lumen inside the cutting cannula.

There are a number of different kinds of valves used in the art for fluid collections systems. One type of valve commonly used is referred to as a "pinch" valve and has an actuator (usually solenoid driven) to pinch shut and release a flexible tubing. A disadvantage of using pinch valves in an automated fluid collection apparatus is the need to use highly flexible, relatively expensive tubing, such as silicone rubber tubing. It is very desirable that the cost of the tubing and other disposable portions of the fluid collection system be minimized to reduce the overall cost of the procedure to the patient. Yet another disadvantage of using pinch valves for an automated biopsy device is the significant time required to position or "thread" the flexible tubing into each pinch valve. This time-consuming step of the fluid collection system set-up usually requires both hands and the full attention of the operator, and there is significant opportunity for error resulting in improper operation of the fluid collection system.

What is needed, therefore, is a fluid collection apparatus for use with an automated biopsy device having at least two vacuum lines, wherein the fluid collection apparatus may be set-up for each patient quickly, easily, and with minimal opportunity for operator error. What is further needed is a fluid collection apparatus in which the disposable portion uses a relatively inexpensive tubing material. What is further needed is a fluid collection apparatus in which each vacuum line is controlled independently and whenever a vacuum source is disconnected from each line, the line is automatically vented to ambient pressure.

SUMMARY OF THE INVENTION

The present invention is a novel fluid collection apparatus for controlling fluid communication between a vacuum source and first and second vacuum lines of a surgical device such as a vacuum-assisted, core sampling, biopsy device. The fluid collection apparatus comprises a first fluid line adapted for detachably connecting to, and in fluid communication with, the first vacuum line. A first valve is in fluid communication with the first fluid line, wherein the first valve has an open and a closed position. When the first valve is in a closed position, fluid communication is blocked between the vacuum source and the first vacuum line, and an air vent is in fluid communication with the first vacuum line. The fluid collection apparatus also comprises a second fluid line adapted for detachably connecting to, and in fluid communication with, the second vacuum line. A second valve is in fluid communication with the second fluid line, wherein the second valve has an open and a closed position. When the second valve is in a closed position, fluid communication is blocked between the vacuum source and the second vacuum line, and the air vent is in fluid communication with the second vacuum line. The fluid collection apparatus further comprises a valve frame fixing the first and second valves relative to each other. The valve frame has a latching means adapted for detachably connecting the valve frame to the surgical device.

In one embodiment of the present invention, a first engagement means is provided for detachably connecting the first valve to an electrically operated first actuator for actuating the first valve between the open and closed positions. A similar second engagement means is provided for detachably connecting the second valve to an electrically operated second actuator for actuating the second valve between the open and closed positions. The first and second actuators are independently controlled by the surgical device according to a predetermined operational sequence. In this embodiment the valve frame fixes the first and second valves so that their longitudinal axes are parallel. When the valve frame is detachably connected to the surgical device, the first and second valves are simultaneously and quickly connected operationally to the first and second actuators, respectively. First and second manual valve controls are also provided. In this embodiment, the fluid collection apparatus also comprises an injection port in at least one of the first and second fluid lines. Also, the first and second valves are rotary valves, which may be used with low cost, medical grade tubing. Also in this embodiment, the first and second actuators are solenoids. Finally, a handle is provided for conveniently and detachably connecting the valve frame to the surgical device in order to connect operationally the first and second valves to the first and second actuators, respectively.

The present invention, therefore, is a disposable, fluid collection apparatus that is quick and easy to set-up for each patient. The present invention also provides the advantage of being adapted for use with inexpensive medical tubing so that cost savings for the overall procedure can be passed on to the patient. The present invention may be used with an automated surgical device having predetermined operational modes according to the steps of the surgical procedure. The present invention provides fluid communication to two separate fluid lines of a surgical device independently of each other and automatically vents to atmosphere each fluid line when fluid communication of that fluid line with a vacuum source is blocked, thus facilitating the removal of tissue samples from the surgical patient.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
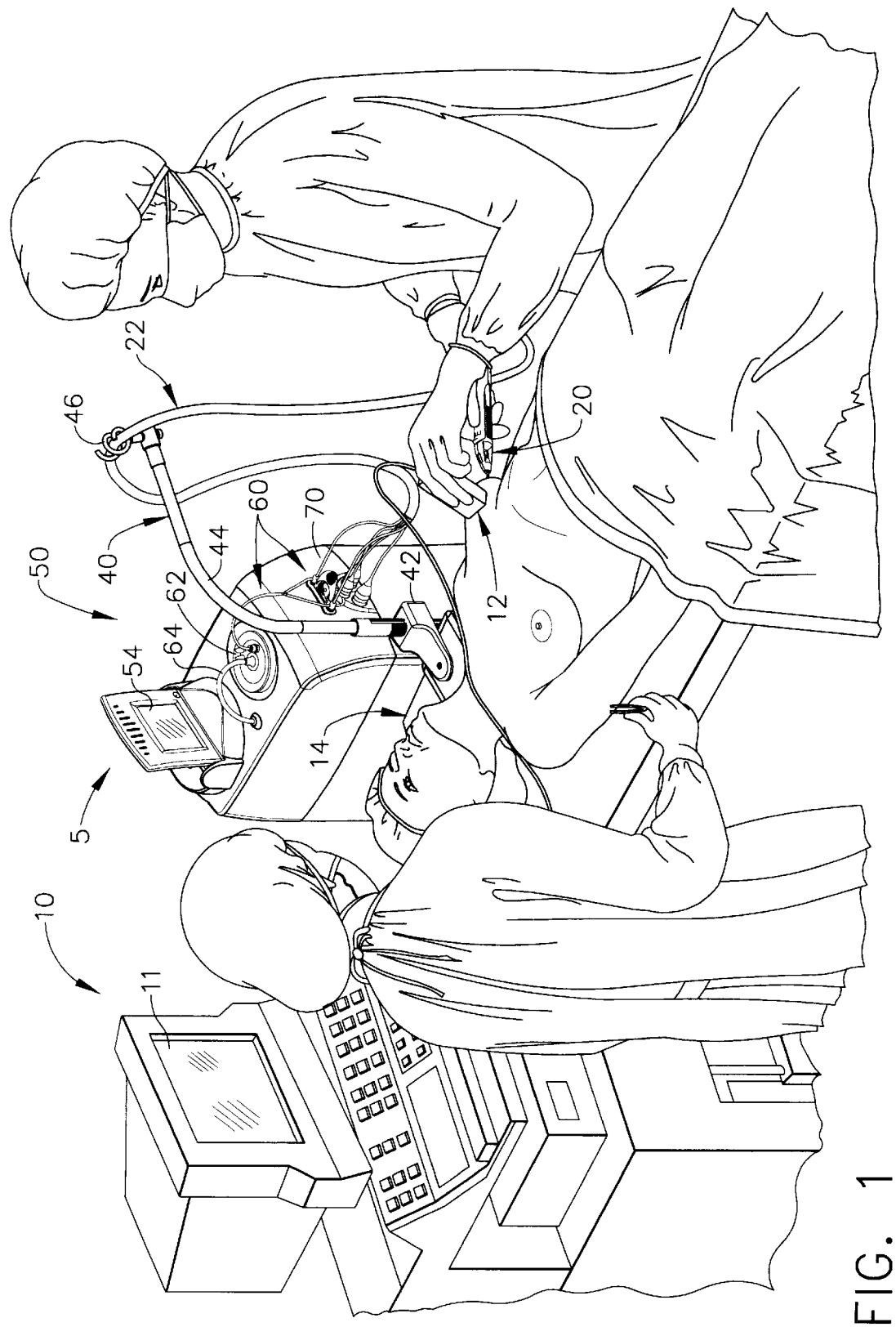
FIG. 1 shows an operator using a biopsy device with the present invention, a fluid collection apparatus, in combination with an ultrasonic imaging device for removing a core tissue sample from a patient.

FIG. 1 shows an operator, an assistant, and a patient who is undergoing a breast biopsy. The operator is using a vacuum assisted, core sampling biopsy device 5 (also referred to as a surgical device) having a handpiece 20 and a control unit 50, which are operatively connected by a cord bundle 22. The operator is using biopsy device 5 in combination with an ultrasonic imaging device 10 having an imaging device handpiece 12 and an imaging device display 11. Imaging device 10 provides a real-time image of lesions, microcalcifications, and high-density masses within the breast tissue of the patient. The operator directs the imaging device handpiece 12 towards suspected tissue masses and guides the distal tip of handpiece 20 of biopsy device 5 adjacent to the suspected tissue for core sampling. Control unit 50 has a display 54 for directing the operator in the sequence of operation of biopsy device 5. A fluid collection system 60 is integrated into control unit 50 for the removal of fluids from handpiece 20. A valve assembly 70 is shown inserted into control unit 50 and is provided for automatically regulating the communication of fluids between handpiece 20 and a vacuum canister 62. A vacuum pump line 64 connected to a vacuum source inside control unit 5 supplies vacuum to vacuum canister 62.

FIG. 1 also shows a bendable arm 40 comprising an arm mount 42 attached to a table 14, a bendable shaft 44, and a pigtail hanger 46 for supporting cord bundle 22. Bendable arm 40 may be bent into different configurations by the operator and supports the weight of cord bundle 22 so that the operator may more easily manipulate handpiece 20.

Figure 2:
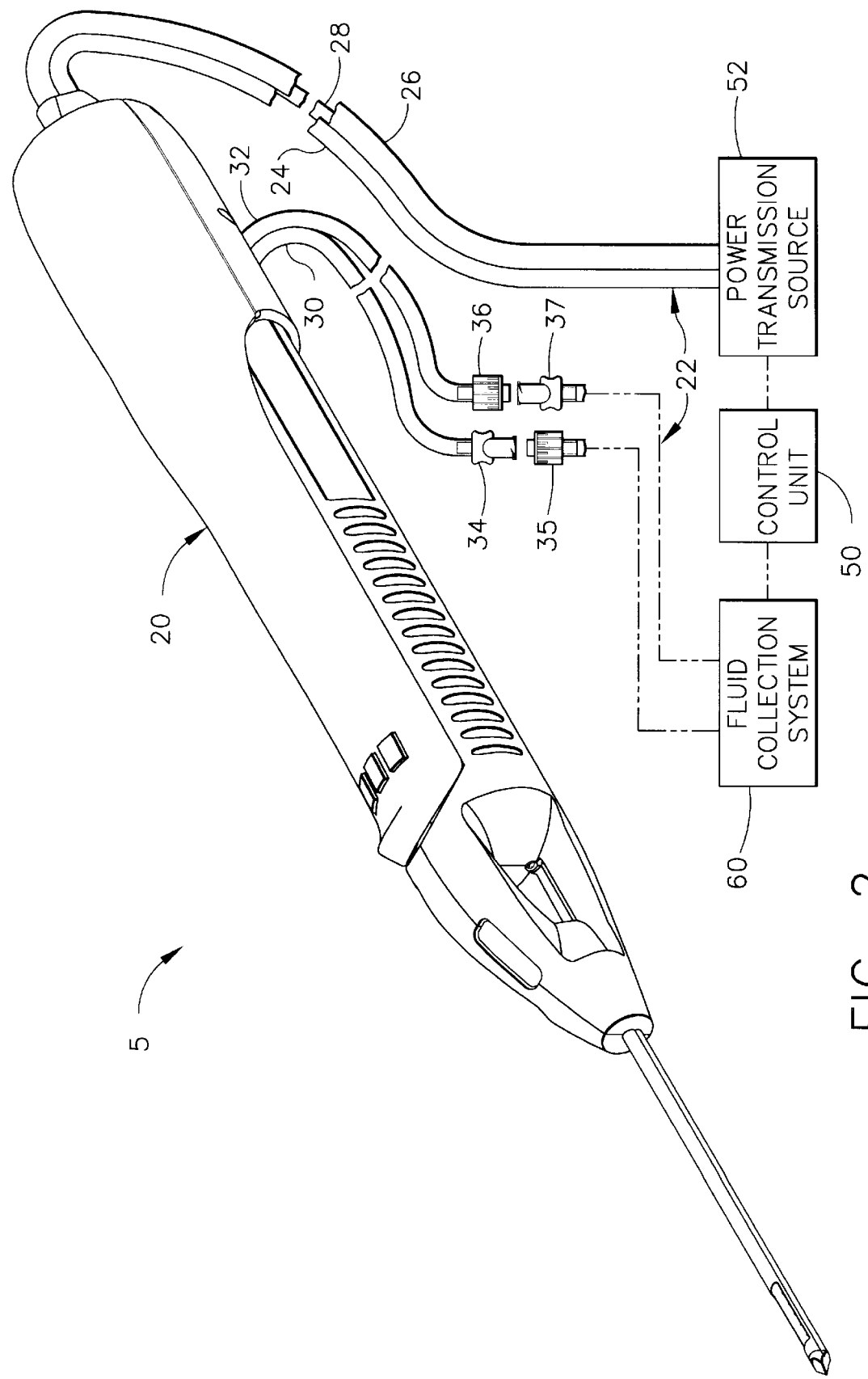
FIG. 2 is an isolated view of the biopsy device shown in FIG. 1, with an isometric view of a handpiece, and with a fluid collection system, a control unit, and a power transmission source shown generically.

FIG. 2 is a view of biopsy device 5 shown in FIG. 1. A complete, detailed description of biopsy device 5 and its method of use is provided in U.S. patent application Ser. No. 09/178,075. Cord bundle 22 contains a control cord 28 for the electrical interface with control unit 50, a first shaft 24 and a second shaft 26 for operatively connecting handpiece 20 to a power transmission source 52 (contained inside of control unit 5), and a first vacuum line 30 and a second vacuum line 32 for fluidly connecting handpiece 20 to fluid collection system 60. First vacuum line 30 and second vacuum line 32 are relatively short (several inches) compared to the overall length of cord bundle 22, and are fluidly coupled to fluid collection system 60 by a first male connector 34, a first female connector 35, a second male connector 36, and a second female connector 37. Cord bundle 22 is bundled together by removable tie wraps or the like and is easily detachable from handpiece fluid collection source 60, control unit 50, and power transmission source 52 in order to clean and/or dispose of handpiece 20.

Figure 3:
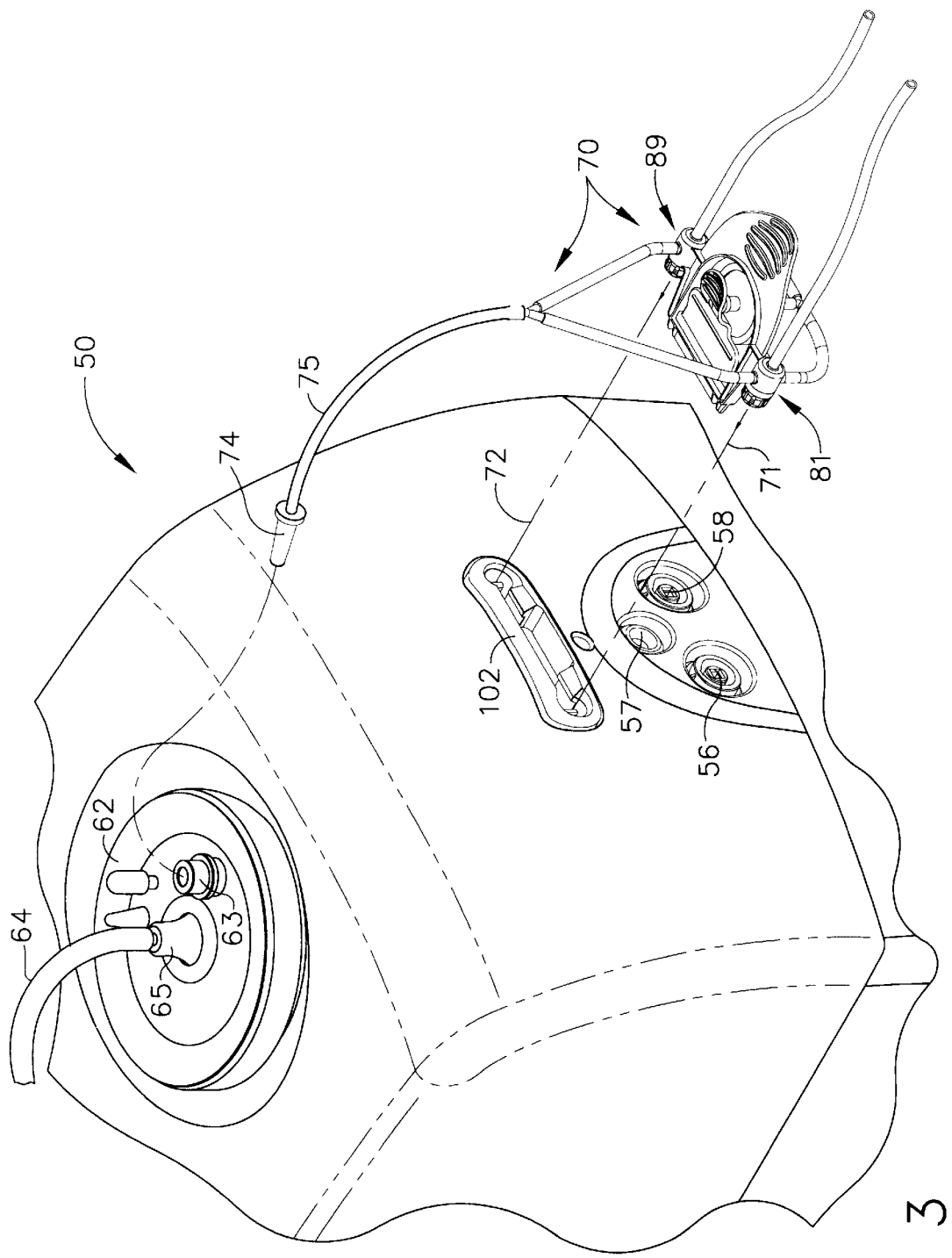
FIG. 3 is a close-up view of a portion of the control unit shown in FIG. 1, and the present invention, a fluid collection apparatus.

FIG. 3 is a close-up, isometric view of a portion of control unit 50 shown in FIG. 1. Valve assembly 70 is shown aligned along a first longitudinal axis 71 and a second longitudinal axis 72 for insertion into a valve receptacle 102 of a valve actuator 100 (not visible) contained within control unit 50. A common distal line 75 having a stem connector 74 fluidly connects valve assembly 70 to a second canister port 63 of vacuum canister 62. Vacuum pump line 64 is fluidly connected to a first canister port 65 of vacuum canister 62. A first power take-off 56 is provided for detachably connecting first shaft 24 (shown in FIG. 2). A second power take-off 58 is provided for detachably connecting second shaft 26 (also shown in FIG. 2). A control cord receptacle 57 is provided for detachably connecting control cord 28 (see FIG. 2).

Still referring to FIG. 3, valve assembly 70 includes a first valve 87 having a first longitudinal axis 71, and a second valve 89 having a second longitudinal axis 72, which is parallel to first longitudinal axis 71. It is necessary for valve assembly 70 to be correctly aligned with valve receptacle 102 in order to insert first valve 87 and second valve 89 into actuator 100 contained within control unit 50. First valve 87 and second valve 89 are rotary valves in this embodiment, although other types of valves may be used in the present invention. First valve 87 is also referred to as a first rotary valve, and second valve 89 is also referred to as a second rotary valve.

Figure 4:
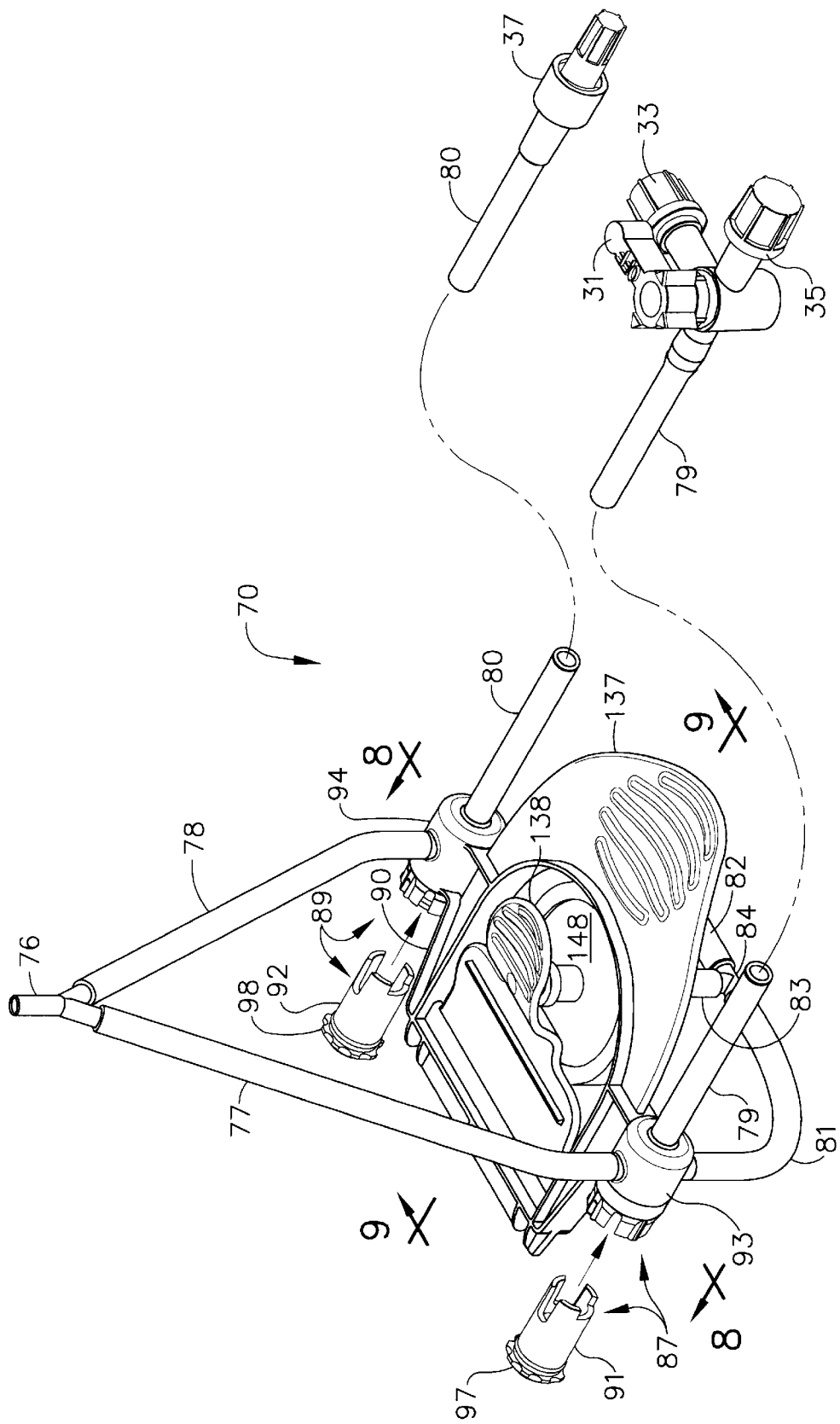
FIG. 4 is an isometric view of a valve assembly of the fluid collection apparatus shown in FIG. 3.

FIG. 4 is an isometric view of valve assembly 70 shown in FIG. 3. First valve 87 and second valve 89 are affixed in parallel alignment onto a valve frame 90 having a valve frame handle 137. Valve assembly 70 further comprises a vent assembly 148 (also referred to as an air vent) affixed to a latch lever 138 cantileverly attached to frame 90 and disposed between first valve 87 and second valve 89. First valve 87 has a first valve spool 91 rotatably inserted into a first valve housing 93. Second valve 89 has a second valve spool 92 rotatably inserted into a second valve housing 94. Valve assembly 70 further comprises a first distal line 77 fluidly connected to first valve 87, and a second distal line 78 fluidly connected to second valve 89. First distal line 77 joins second distal line 78 at a Y-connector 76, which is fluidly connected to common distal line 75 shown in FIG. 3. Valve assembly 70 further comprises a first vent line 81 fluidly connected to first valve 87, and a second vent line 82 fluidly connected to second valve 89. First vent line 81 and second vent line 82 join at a T-connector 84, which is fluidly connected by a common vent line 83 to vent 148.

Valve frame 90, first valve 87, second valve 89, latch lever 138, and valve handle 137 may be made from a medical grade, rigid, injection molded plastic such as polycarbonate. All of the fluid carrying lines described for valve assembly 70 (including first distal line 77, second distal line 78, first fluid line 79, second fluid line 80, first vent line 81, second vent line 82, common vent line 83) may be made of an economical, flexible, medical grade material such as polyvinyl chloride (PVC). First valve spool 91 and second valve spool 92 are preferably made from a rigid, medical grade plastic such as polyethylene.

First vacuum line 30 of handpiece 20 shown in FIG. 2 is fluidly connected to first valve 87 via a first fluid line 79, shown in FIG. 4. As shown in FIG. 4, female connector 35 has a injection port 33, which is fluidly connectable to first vacuum line 30 by actuation of a 3-way valve 31. Injection port 33 provides the operator a convenient place to inject solutions such as lidocaine for local anesthesia into the tissue of the patient. Second vacuum line 32 of biopsy device 5 shown in FIG. 2 is fluidly connected to second valve 89 via a second fluid line 80 shown in FIG. 4.

In the embodiment shown in FIG. 4 for the valve assembly 70, first valve 87 and second valve 89 are rotational type valves. This type of valve provides numerous advantages over other types of valves such as, for example, pinch valves. One advantage is ease of setting up the fluid collection system by the operator. For pinch valves it is necessary to insert a portion of flexible tubing between the actuators of the pinch valve so that the actuators can close and open the tubing during operation. This set-up procedure can be difficult and time-consuming for some operators. In addition, pinch valves must be used with a medical grade, flexible tubing made from a relatively expensive material such as silicone rubber in order to withstand the many cycles of opening and closing without breakage. As will be described, the valve assembly of the present invention can be used with inexpensive medical tubing and can be quickly set-up with one hand.

Figure 6:
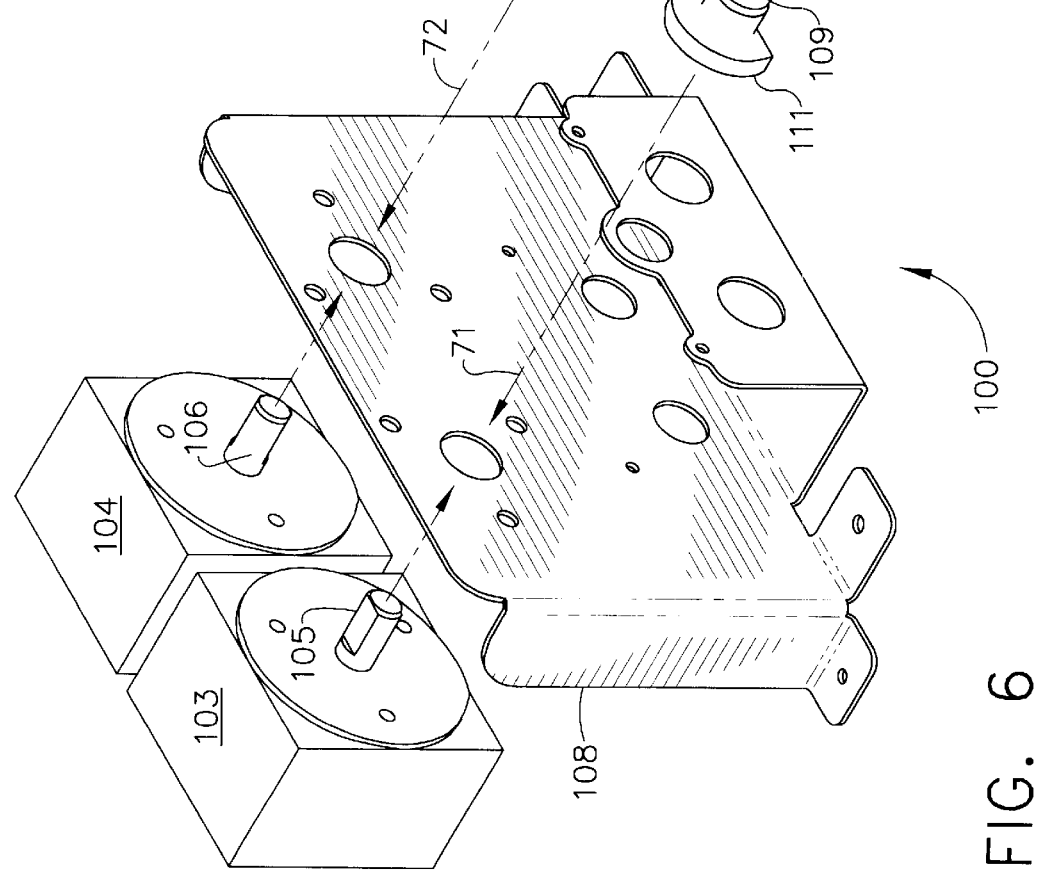
FIG. 6 is an exploded view of a valve actuator of the fluid collection apparatus shown in FIG. 3.

FIG. 6 is an exploded view of actuator 100, which was described earlier for FIG. 3 as being contained within control unit 50. First spool 91 and second spool 92 of valve assembly 70 (FIG. 4) are shown in alignment for insertion into valve receptacle 102. Actuator 100 drives first valve 87 and second valve 89 according to a predetermined sequence to control the flow of fluids through valve assembly 70 during the biopsy procedure. This predetermined sequence is programmed into the control unit 50 so that either a negative (vacuum) or an ambient (atmospheric) pressure is supplied to each of the lines, 30 and 32, to handpiece 20. A full description of this control method and the operational modes of biopsy device 5 are found in U.S. patent application Ser. No. 09/282140. In FIG. 6, actuator 100 comprises a first solenoid 103 (also referred to as a first actuator) and a second solenoid 104 (also referred to as a second actuator), which are mounted on a formed metal, actuator frame 108. First and second solenoids, 103 and 104, are of the rotary type and a suitable example for each is available from Kuhnke Automation, Inc. as part number E76-ROL-F-D57541-24DC-80% ED. First and second solenoids, 103 and 104, respond independently to commands from control unit 5.

First solenoid 103 is activated and a first solenoid shaft 105 rotates a partial turn in response to an electronic signal from the control unit 5. A return spring (not visible) inside of first solenoid 103 causes first solenoid shaft 105 to rotate to the original position when first solenoid 103 is deactivated in response to control unit 5. A first coupling 109 is attached to first solenoid shaft 105 by a setscrew (not shown) or the like. Similarly, a second coupling 110 is attached to a second solenoid shaft 106 of second solenoid 104. First coupling 109 has a wedge-shaped, first lobe 111 attached to its proximal end and a rectangularly shaped tab 113 extending from its distal end. Second coupling 110 has a wedge-shaped, second lobe 112 attached to its proximal end and a rectangularly shaped tab 114 extending from its distal end.

Still referring to FIG. 6, valve receptacle 102 has a bolt flange 118 for attachment to actuator frame 108 with screw fasteners (not shown). Valve receptacle further includes a sleeve 120 extending from bolt flange 118. When assembled, first coupling 109 rotatably protrudes into a first bore 121 of sleeve 120 and second coupling 110 rotatably protrudes into a second bore 122 of sleeve 120. A first O-ring 115 seals the radial clearance space between first coupling 109 and first bore 121. A second O-ring 116 seals the radial clearance space between second coupling 110 and second bore 122.

FIG. 6 also shows a second spring 117 and a first spring 119, which are spaced laterally apart and assembled to valve receptacle 102 using a second screw 147 and a first screw 149, respectively. Springs 117, 119 are identical, compression, helical coil type springs and are made preferably of stainless steel. Second and first springs, 117 and 119, are provided to assist the operator in properly aligning and engaging valve assembly 70 into valve receptacle 102.

Figure 5:
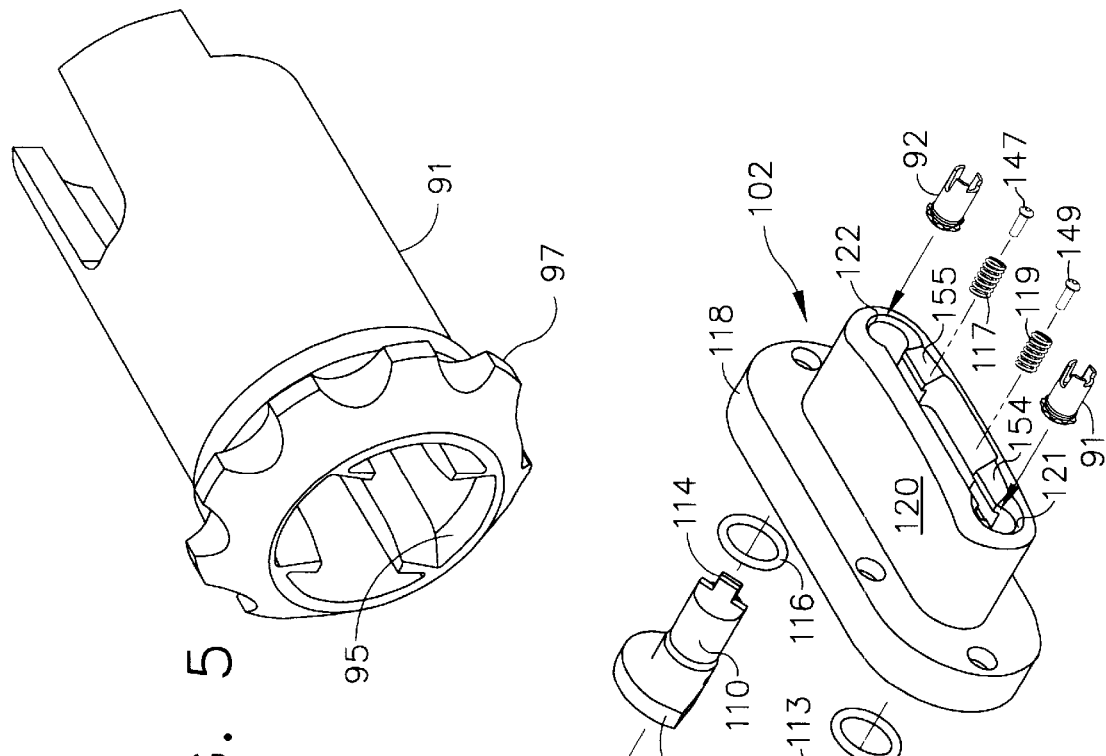
FIG. 5 is an enlarged, isometric view of a spool of a valve of the valve assembly shown in FIG. 4.

FIG. 5 is an enlarged view of the proximal end of first spool 91 of first valve 87. A first keyslot 95 is formed into the distal end for operational engagement with first tab 113 of first coupling 109. When valve assembly 70 is fully inserted into valve receptacle 102 as described for FIG. 3, first tab 113 is operationally engaged with first keyslot 95. Rotation of first solenoid 103 in one direction, therefore, rotates spool 91 into an open position so that vacuum is supplied to first vacuum line 30 of handpiece 20 (see FIG. 2). Rotation of first solenoid 103 in the opposite direction (back to its original position) rotates spool 91 into an closed position so that vacuum is not supplied to first vacuum line 30, but instead first vacuum line 30 is vented. Similarly, second tab 114 of coupling 110 engages with a keyslot (not shown) in second spool 92 of second valve 89. Rotation of second solenoid 104 in one direction rotates spool 92 into an open position so that vacuum is supplied to second vacuum line 32 of handpiece 20. Rotation of second solenoid 104 in the opposite direction rotates spool 92 into an closed position so that second vacuum line 32 is vented.

First keyslot 95 of first spool 91 (shown in FIG. 5) and first tab 113 of first coupling 109 (shown in FIG. 6) constitute an example of what is also referred to as a first engagement means.

Other embodiments of the first engagement means are possible, such as a spline type of engagement means. Second keyslot (not shown) of spool 110 and second tab of second coupling 110 constitute an example of what is also referred to as a second engagement means. Again, other embodiments are possible, as is evident to those skilled in the art.

As shown in FIG. 5, a first fluted knob 97 (also referred to as a first manual control) is provided on first spool 91 for manual operation of first valve 87. First fluted knob 97 allows the operator to actuate the first valve 87 independently of control unit 5, as may be required, for example, if first keyslot 95 of first valve spool 91 is not properly aligned with first tab 113 of first coupling 109 when attaching valve assembly 70 to valve actuator 100. A second fluted knob 98 (also referred to as a second manual control) is shown in FIG. 4 and is provided for manual operation of second valve 89.

Figure 7:
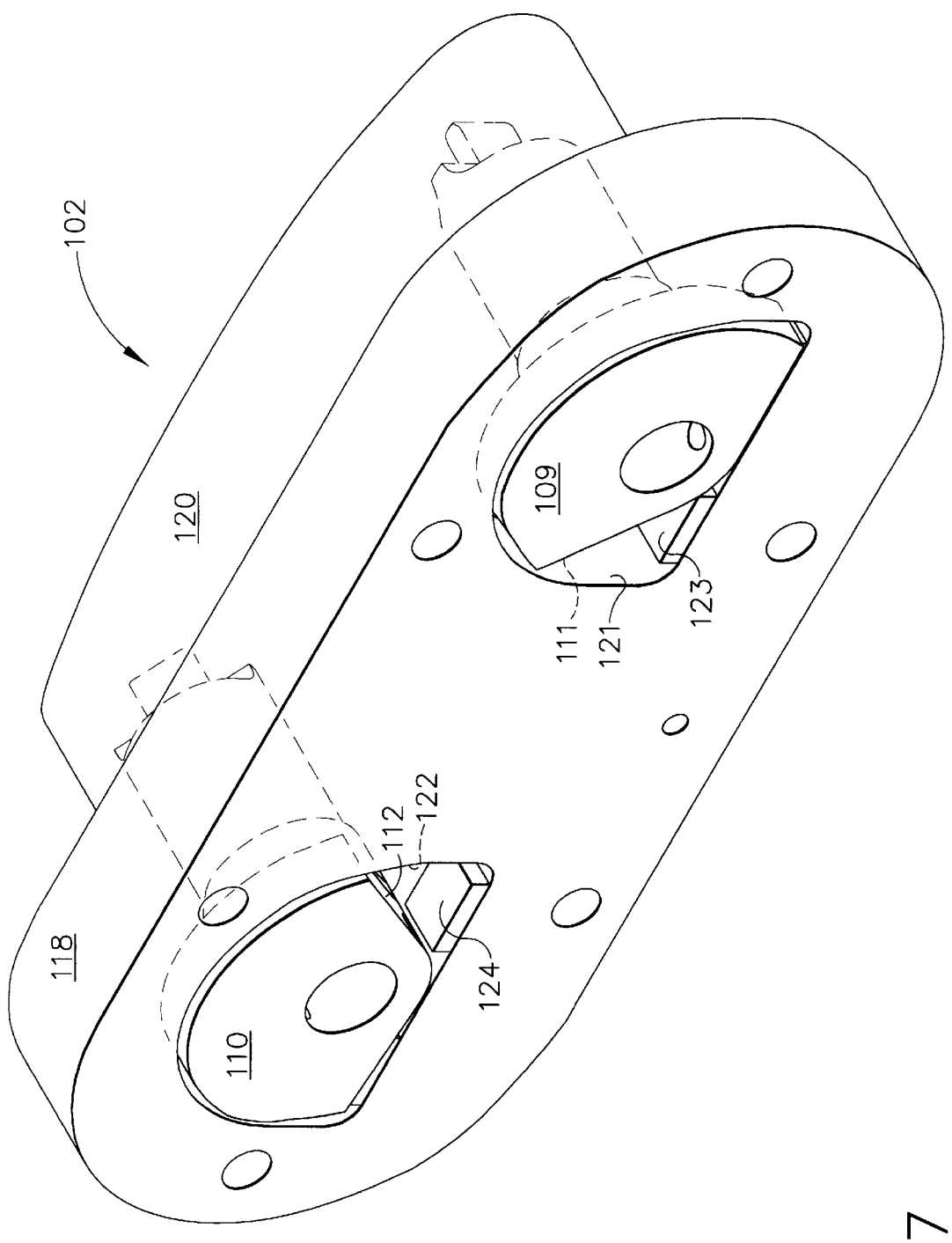
FIG. 7 is an enlarged isometric view of a valve receptacle of the valve actuator shown in FIG. 6.

FIG. 7 is an enlarged view of the proximal side of valve receptacle 102. First coupling 109 is shown located inside of first bore 121 as it would be when valve assembly 70 is fully inserted into valve receptacle 102. Similarly, second coupling 110 is shown located inside of second bore 122. When viewed from this side, first lobe 111 is rotated to a full, clockwise position, and second lobe 112 is rotated to a full, counterclockwise direction. Two first stop cushions 123 made of a resilient material such as sponge rubber are adhered to valve receptacle 102 to cushion the rotational movements of lobe 111. Two second stop cushions 124 are similarly attached to valve receptacle 102 to cushion the rotational movements of lobe 112. First and second stop cushions, 123 and 124, are provided primarily to limit the rotational movement of spools, 91 and 92, into the open or closed positions. By being made of a resilient material such as a sponge rubber, cushions 123 and 124 also reduce the noise and wear associated with the impact of lobes 111 and 112 with valve receptacle 102.

Figure 8:
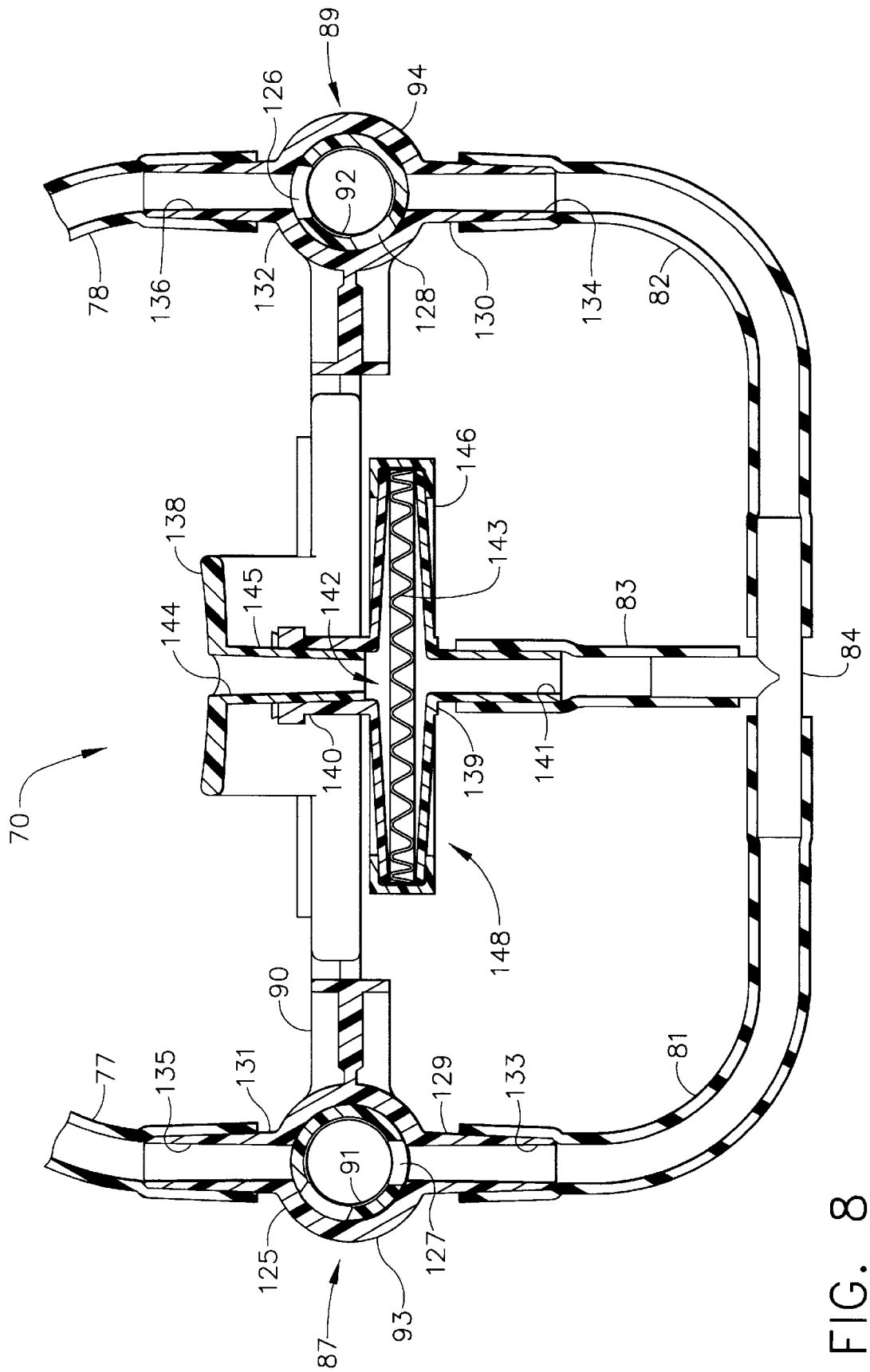
FIG. 8 is a sectional view taken along line 8—8 of the valve assembly shown in FIG. 4.

FIG. 8 is a sectional view of valve assembly 70 shown in FIG. 4 and taken along line 8—8. The valve positions shown in FIG. 8 correspond with the lobe positions shown in FIG. 7. First valve 87 is shown in the closed position for when first vacuum line 30 of handpiece 20 (see FIG. 2) is vented to atmosphere. Second valve 89 is shown in the open position for when second vacuum line 32 of handpiece 20 (see FIG. 2) is connected to vacuum. First spool 91 has a first vent passage 127 and a first fluid passage 125. Second spool 92 has a second vent passage 128 and a second fluid passage 126.

Figure 11:
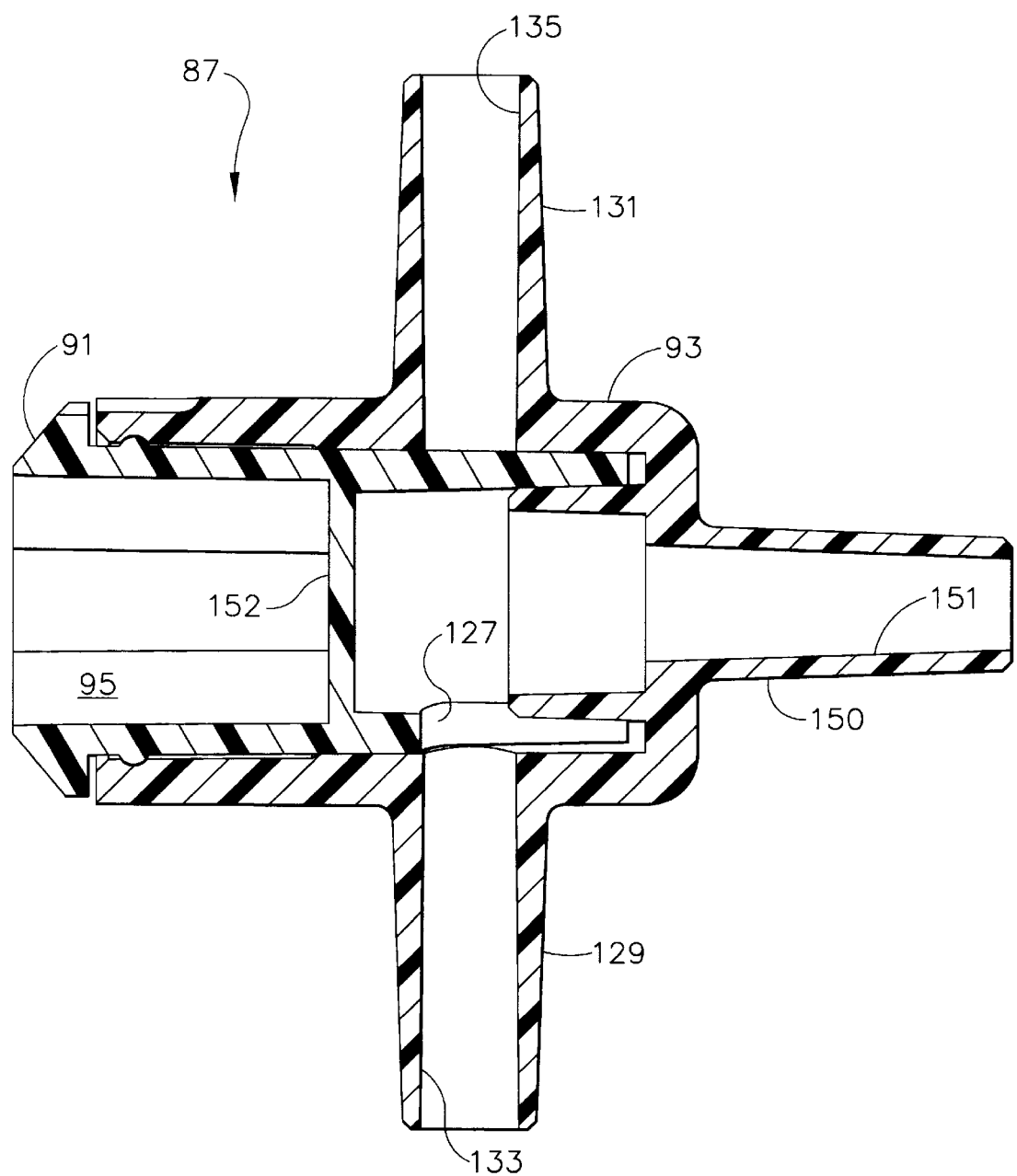
FIG. 11 is a sectional view of a valve spool and a valve housing of the valve assembly shown in FIG. 4.

FIG. 11 is a sectional view taken through the longitudinal axis of first valve 87 in the closed position. First housing 93 has a first upper stem 131 with a first upper lumen 135 (vacuum supply), a first middle stem 150 with a first middle lumen 151 (connected to first vacuum line 30 of handpiece 20), and a first lower stem 129 with a first lower lumen 133 (vent). First spool 91 is shown with first vent passage 127 fluidly connecting first lower lumen 133 to first middle lumen 151, while first upper lumen is closed off. A dividing wall 152 inside of first spool 91 seals first keyslot 95 from the fluid carrying portions of first valve 87. Second valve 89 is identical in construction and operation to first valve 87.

Returning to FIG. 8, first valve 87 is shown with first upper stem 131 having first upper lumen 131 blocked from first lower lumen 133 of first lower stem 129. For second valve 89, a second upper lumen 136 of a second upper stem 132 is opened into spool 92 to allow fluid flow into second vacuum line 32 of handpiece 20 (see FIG. 2) via a second middle lumen of a second middle stem (not shown). A second lower lumen 134 of a second lower stem 130 is blocked from inside of spool 92.

Vent assembly 148 comprises a disc-shaped, vent chamber housing 146 with a lower vent stem 139 and an upper vent stem 140 extending therefrom. Vent chamber 146, lower vent stem 139, and upper vent stem 140 are made from a rigid, medical grade plastic such as an acrylic polymer. Inside of vent chamber housing 146 is vent chamber 143 containing a filter 143, which prevents liquids and particulate matter from being sprayed out of the valve assembly 70, or from atmospheric particulate matter being drawn into the system. Filter 143 may be made of a modified acrylic copolymer polyamide, for example, such as VERSAPOR 200R available from Pall Medical, Inc., Ann Arbor, Mich. Upper vent stem 140 is attached to a upper vent coupling 145 having a lumen 144 and extending from latch lever 138. Vent assembly 148 moves slightly up and down when the latch lever 138 is actuated as will be described, and is permitted by the flexibility of first and second vent lines, 81 and 82 respectively.

Figure 9:
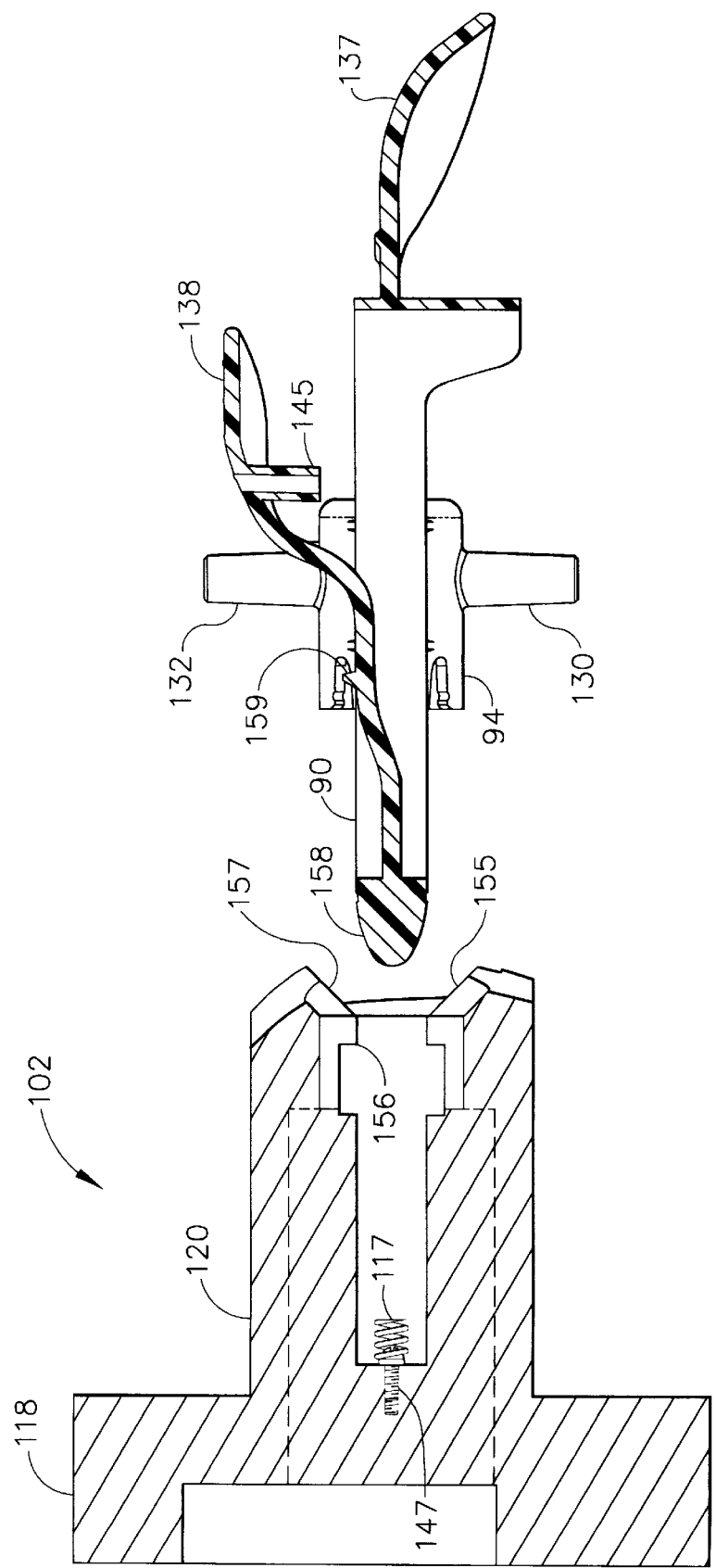
FIG. 9 is a sectional view taken along line 9—9 of the valve assembly shown in FIG. 4 aligned for insertion into the valve receptacle shown in FIG. 6.
Figure 10:
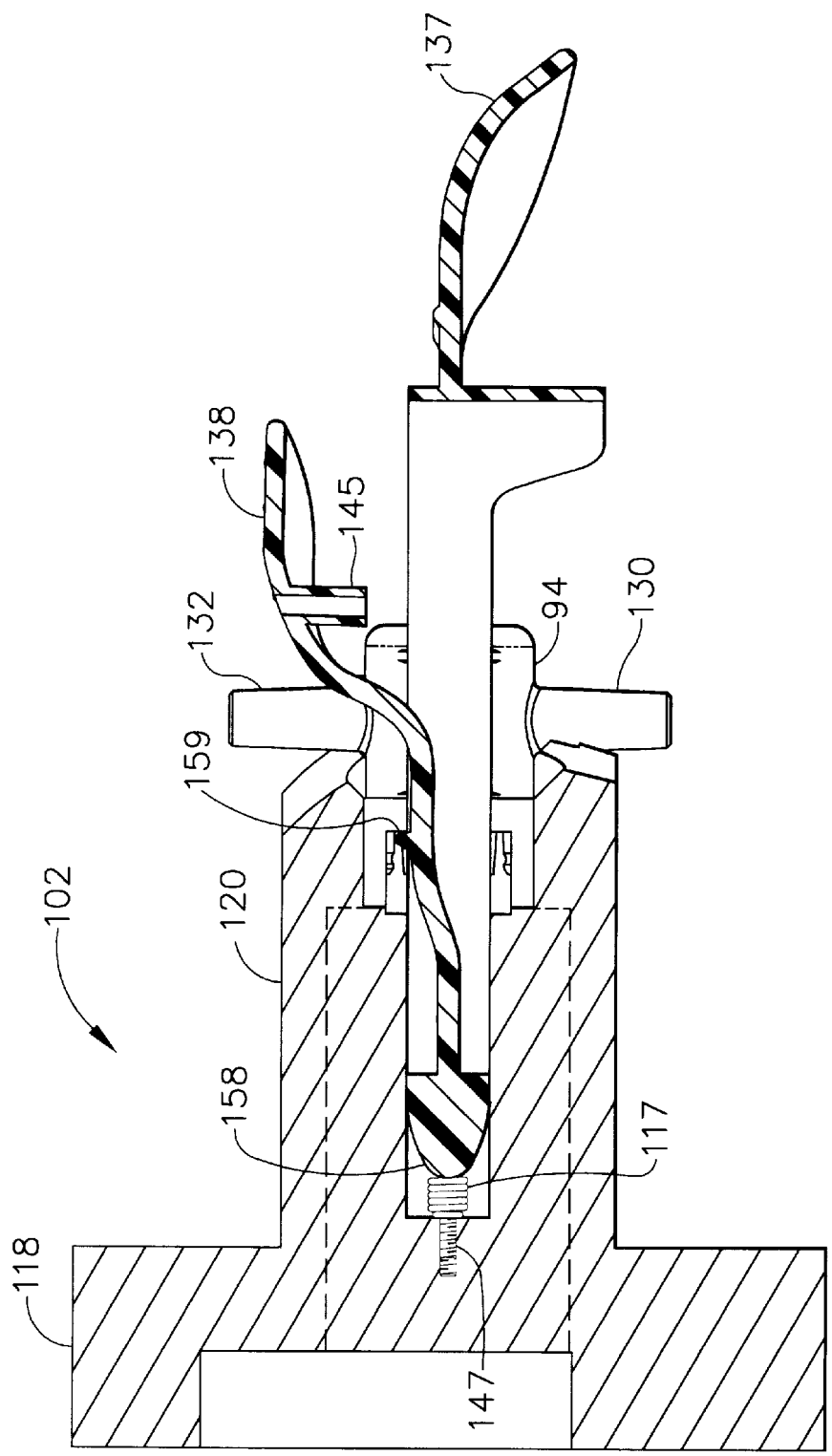
FIG. 10 is the same view as FIG. 9, but for when the valve assembly is fully engaged into the valve receptacle.

FIGS. 9 and 10 show how valve assembly 70 is retained inside of valve receptacle 102. A sectional view of valve receptacle 102 shows a right lower ramp 155 (also shown in FIG. 2) and an upper ramp 157, together which guide a valve frame nose 158 of valve frame 90 into sleeve 120 of valve receptacle 102. When the operator grasps handle 137 and fully inserts valve assembly 70 into valve receptacle 120, a latch 159 extending from latch lever 138 engages with a latching ledge 156 on the inside of valve receptacle 102. The operator may do this with one hand, but the valve assembly 70 must be aligned with the valve receptacle 102 as described for FIG. 3. Concurrently, upper ramp 157 and a left lower ramp 154 (see FIG. 4) guide valve frame nose 158. By depressing latch lever 138 while holding handle 137 with the same hand, the operator may pull valve assembly 70 out of valve receptacle 102.

A beneficial aspect of the present invention is that valve assembly 70 may be inserted into valve receptacle 102 with one hand. In addition, when valve assembly 70 is fully inserted for proper operation, there is audible feedback (a clicking sound) due to the interaction of latching ledge 156 and valve receptacle 102. This audible feedback cues the user that the valve assembly 70 is properly inserted for operation.

FIGS. 9 and 10 also illustrate how second spring 117 is compressed by the insertion of valve assembly 70. First spring 119 is compressed in a like manner, but is not shown in FIGS. 9 and 10. As nose 158 of valve assembly 70 is pushed into valve receptacle 102, second spring 117 and first spring 119 exert a small force in the opposite direction onto nose 158. If the operator attempts to insert valve assembly 70 while first valve axis 71 and second valve axis 72 are not aligned with valve receptacle as shown in FIG. 3, then second and first springs, 117 and 119, will tend to realign valve assembly 70 into the proper orientation for insertion. Second and first springs, 117 and 119, also help to eject valve assembly 70 when it is not fully engaged into valve receptacle 102 for proper operation, or when it is desired to remove valve assembly 70 from valve receptacle 102.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that only the spirit and scope of the appended claims limit the invention.

What is claimed is:

1. A fluid collection apparatus for controlling fluid communication between a vacuum source and first and second vacuum lines of a surgical device, said fluid collection apparatus comprising:
 a. a first fluid line adapted for detachably connecting to, and in fluid communication with, said first vacuum line;
 b. a second fluid line adapted for detachably connecting to, and in fluid communication with, said second vacuum line;
 c. a first valve having a first longitudinal axis, said first valve in fluid communication with said first fluid line, wherein said first valve has an open position and a closed position;
 d. a second valve having a second longitudinal axis, said second valve in fluid communication with said second fluid line, wherein said second valve has an open position and a closed position;
 e. an air vent selectively communicating with said first and second fluid lines, and when said first valve is in said closed position and said first and second fluid lines are connected to said first and second vacuum lines, fluid communication is blocked between said vacuum source and said first vacuum line, and said air vent is in fluid communication with said first vacuum line, and when said second valve is in said closed position and said first and second fluid lines are connected to said first and second vacuum lines, fluid communication is blocked between said vacuum source and said second vacuum line, and said air vent is in fluid communication with said second vacuum line; and
 f. a valve frame fixing said first and second valves relative to each other, said valve frame having a latching means adapted for detachably connecting said valve frame to said surgical device.

2. The fluid collection apparatus of claim 1 further comprising a first engagement means attached to said first valve and adapted for detachably and operationally connecting said first valve to an electrically operated first actuator of said surgical device for actuating said first valve between said open and closed positions, and a second engagement means attached to said second valve and adapted for detachably and operationally connecting said second valve to an electrically operated second actuator of said surgical device for actuating said second valve between said open and closed positions.

3. The fluid collection apparatus of claim 2 wherein said valve frame fixes said first and second valves so that said first longitudinal axis of said first valve is parallel to said second longitudinal axis of said second valve, and when said valve frame is detachably connected to said surgical device, said first and second valves are simultaneously connected operationally to said first and second actuators.

4. The fluid collection apparatus of claim 3 wherein said first actuator is a first solenoid and said second actuator is a second solenoid.

5. The fluid collection apparatus of claim 4 wherein said first solenoid and said second solenoid are controlled independently of each other.

6. The fluid collection apparatus of claim 5 wherein said first valve includes a first manual control and said second valve includes a second manual control.

7. The fluid collection apparatus of claim 1 further comprising an injection port in at least one of said first and second fluid lines.

8. The fluid collection apparatus of claim 1 wherein said first valve is a first rotary valve and said second valve is a second rotary valve.

9. The fluid collection apparatus of claim 1 wherein said air vent includes a filter.

10. The fluid collection apparatus of claim 1 wherein said valve frame includes a handle for holding said valve frame while detachably connecting said valve frame to said surgical device.

\* \* \* \* \*